(12) United States Patent
Fan et al.

(10) Patent No.: US 11,305,265 B2
(45) Date of Patent: Apr. 19, 2022

(54) AROMATIZATION CATALYST AND PREPARATION PROCESS AND USE THEREOF

(71) Applicants: Institute of Coal Chemistry, Chinese Academy of Sciences, Taiyuan (CN); Shanxi Lu'an Mining (Group) Co., Ltd., Changzhi (CN)

(72) Inventors: Weibin Fan, Taiyuan (CN); Dezhi Shi, Taiyuan (CN); Huaqing Zhu, Taiyuan (CN); Mei Dong, Taiyuan (CN); Jianguo Wang, Taiyuan (CN); Zhiwei Wu, Taiyuan (CN); Weiyong Jiao, Taiyuan (CN); Junyi Liu, Changzhi (CN); Dongfei Wang, Changzhi (CN); Jinbo Li, Changzhi (CN); Yanbin Cui, Changzhi (CN); Yibo Zhang, Changzhi (CN)

(73) Assignees: Institute of Coal Chemistry, Chinese Academy of Sciences, Taiyuan (CN); Shanxi Lu'an Mining (Group) Co., Ltd., Changzhi (CN)

( * ) Notice: Subject to any disclaimer, the term of this patent is extended or adjusted under 35 U.S.C. 154(b) by 0 days.

(21) Appl. No.: 16/994,113

(22) Filed: Aug. 14, 2020

(65) Prior Publication Data
US 2021/0213432 A1    Jul. 15, 2021

(30) Foreign Application Priority Data
Jan. 13, 2020    (CN) ........................ 202010030766.X

(51) Int. Cl.
| | |
|---|---|
| *C07C 2/84* | (2006.01) |
| *B01J 29/40* | (2006.01) |
| *B01J 23/18* | (2006.01) |
| *B01J 35/00* | (2006.01) |
| *B01J 37/04* | (2006.01) |
| *B01J 37/08* | (2006.01) |
| *C07C 2/06* | (2006.01) |
| *C07C 2/08* | (2006.01) |
| *C07C 2/10* | (2006.01) |
| *C07C 2/04* | (2006.01) |
| *C07C 2/12* | (2006.01) |
| *C07C 2/76* | (2006.01) |
| *C07C 15/06* | (2006.01) |
| *C07C 15/08* | (2006.01) |
| *B01J 35/10* | (2006.01) |

(52) U.S. Cl.
CPC .............. *B01J 29/405* (2013.01); *B01J 23/18* (2013.01); *B01J 35/0053* (2013.01); *B01J 37/04* (2013.01); *B01J 37/082* (2013.01); *C07C 2/04* (2013.01); *C07C 2/06* (2013.01); *C07C 2/08* (2013.01); *C07C 2/10* (2013.01); *C07C 2/12* (2013.01); *C07C 2/76* (2013.01); *C07C 2/84* (2013.01); *C07C 15/06* (2013.01); *C07C 15/08* (2013.01); *B01J 35/1057* (2013.01); *B01J 35/1061* (2013.01); *B01J 35/1066* (2013.01); *B01J 35/1071* (2013.01); *B01J 35/1076* (2013.01); *B01J 35/1095* (2013.01); *B01J 2229/183* (2013.01); *B01J 2229/186* (2013.01); *B01J 2229/42* (2013.01); *C07C 2529/40* (2013.01); *Y02P 20/52* (2015.11)

(58) Field of Classification Search
CPC ... Y02P 20/52; C07C 2/84; C07C 2/76; C07C 2/04; C07C 2/06; C07C 2/08; C07C 2/10; C07C 2/12; C07C 2529/40; C07C 15/04; C07C 15/06; C07C 15/08; B01J 29/041; B01J 29/40; B01J 35/1095; B01J 35/1076; B01J 35/1057; B01J 35/1061; B01J 35/1066; B01J 35/107; B01J 35/1071
USPC .......................................... 585/407, 415, 486
See application file for complete search history.

(56) References Cited

U.S. PATENT DOCUMENTS

| | | | |
|---|---|---|---|
| 4,175,057 A | 11/1979 | Davies et al. | |
| 7,164,052 B2 * | 1/2007 | Carati ...................... | B01J 29/40 585/418 |
| 2011/0124933 A1 * | 5/2011 | Kiesslich .................. | C07C 2/76 585/417 |
| 2019/0030519 A1 * | 1/2019 | Wattanakit ............ | C01B 39/065 |

FOREIGN PATENT DOCUMENTS

| | | |
|---|---|---|
| CN | 1938245 A | 3/2007 |
| CN | 102872901 A | 1/2013 |

* cited by examiner

*Primary Examiner* — Elizabeth D Wood
(74) *Attorney, Agent, or Firm* — Harness, Dickey & Pierce, P.L.C.

(57) ABSTRACT

An aromatization catalyst and preparation process and use thereof is set forth. The catalyst comprises an inorganic oxide and a modified Ga-ZSM-5 zeolite, which comprises a modified ZSM-5 zeolite with a hierarchical macro-meso-microporosity and gallium deposited in channels of and/or on surfaces of the modified ZSM-5 zeolite. The hierarchical porosity of the modified ZSM-5 zeolite in the catalyst can reduce diffusion resistance of products during the aromatization reaction, thereby retarding carbon depositing rate and substantially improving catalytic activity, aromatic hydrocarbon selectivity, stability and lifetime of the catalyst. When being used in aromatization of propane, the catalyst exhibits a high stability, a lifetime of more than 320 hours, and a selectivity to aromatic hydrocarbons of up to 73.3 wt. %.

4 Claims, 4 Drawing Sheets

AROMATIZATION CATALYST AND PREPARATION PROCESS AND USE THEREOF

CROSS-REFERENCE TO RELATED APPLICATION

This application claims the benefit and priority of Chinese Application No. 202010030766X, filed Jan. 13, 2020. The entire disclosure of the above application is incorporated herein by reference.

FIELD

The present disclosure generally relates to the field of catalysts, and in particular to an aromatization catalyst and a process for preparing the same, as well as the use thereof for aromatization of a lower alkane.

BACKGROUND

Aromatic hydrocarbons are an important raw material in organic chemical industry, and their annual consumption in China is huge currently. Conversion of abundant and cheap lower alkanes into benzene, toluene, and xylene with a high additional value has become an important research hotspot in the past 30 years.

Commonly used catalysts for aromatization of lower alkanes include supported metal catalysts, such as $Pt/Al_2CO_3$ and $Cr_2O_3/Al_2CO_3$ and zeolite-type catalysts such as MFI, MCM, and L type zeolites, the one that has been subjected to more studies recently is ZSM-5 zeolite.

CN 1938245 describes a Pt/Ga-ZSM-5 zeolite catalyst having a MFI structure, used for aromatization of C2-C6 alkanes. In the case of propane, the catalyst can provide a selectivity to aromatic hydrocarbons of only around 30 to 40%.

U.S. Pat. No. 4,175,057 describes a zinc, gallium, and copper supported ZSM-5 zeolite catalyst. It has been found that when the catalyst is used for the aromatization of propane and butane, the selectivity to aromatic hydrocarbons is only around 30 to 40%.

CN 102872901 B describes an aromatization catalyst, which is a metal-modified HZSM-5. The catalyst is only suitable for the aromatization of C4-C6 alkanes, and can provide a yield of aromatic hydrocarbons of only around 45%.

From above, it can be seen that the most studied catalysts for the aromatization of lower alkanes are ZSM-5 zeolites on which a metal(s) such as gallium (Ga), zinc (Zn), and platinum (Pt) has been deposited. Among these zeolites, gallium-modified ZSM-5 has a higher catalytic activity for the aromatization of the lower alkanes. However, there are still some problems with the gallium-modified ZSM-5 zeolite catalysts, for example, the selectivity to aromatic hydrocarbons, the lifetime and thermal stability of the catalyst should be further improved.

SUMMARY

An objective of the disclosure is to provide an aromatization catalyst which has an increased gallium dispersion and exhibits an excellent catalytic activity for aromatization of lower alkanes, a high selectivity to aromatic hydrocarbons, good thermal stability and a long lifetime.

This objective of the disclosure is realized by an aromatization catalyst comprising an inorganic oxide and a modified Ga-ZSM-5 zeolite, which comprises a modified ZSM-5 zeolite with a hierarchical macro-meso-microporosity and gallium deposited in channels of and/or on surfaces of the modified ZSM-5 zeolite.

The modified Ga-ZSM-5 zeolite may have a gallium loading of about 0.1 wt. % to about 5 wt. %.

The mass of the modified Ga-ZSM-5 zeolite may be about 30% to about 85% of the mass of the catalyst.

The catalyst may have a specific surface area of about 250 $m^2/g$ to about 550 $m^2/g$.

The present disclosure further provides a process for preparing the aromatization catalyst as described hereinabove, comprising steps of:

(a) adding a silicon source into a mixed aqueous solution containing an aluminum source and a first structure directing agent to perform a hydrothermal reaction so as to obtain a first solid product, which is then subjected to calcination to obtain a ZSM-5 zeolite precursor;

(b) mixing the ZSM-5 zeolite precursor with water and a second structure directing agent together to perform a hydrothermal treatment so as to obtain a second solid product, which is then subjected to calcination;

(c) subjecting a product resulting from the calcination in step (b) to an alkali treatment so as to obtain a hierarchical ZSM-5 zeolite;

(d) subjecting the obtained zeolite to be modified with ammonium ions and then calcined to obtain a modified ZSM-5 zeolite;

(e) subjecting the modified ZSM-5 zeolite to be ion-exchanged with a solution of gallium salt and then to be calcined to obtain a modified Ga-ZSM-5 zeolite; and (f) mixing the modified Ga-ZSM-5 zeolite with an inorganic oxide precursor, followed by shaping, drying, and then calcination, to yield the aromatization catalyst.

The hydrothermal reaction in step (a) is preferably performed at a temperature of about 120° C. to about 200° C. for about one day to about six days. The hydrothermal treatment in step (b) is preferably performed for about one day to about four days.

In step (a), a molar ratio of the silicon source to the aluminum source is preferably equal to or greater than about 20:1, a molar ratio of the water to the silicon source is preferably from about 10:1 to about 100:1, and a molar ratio of the silicon source to the first structure directing agent is preferably from about 1:0.1 to about 1:0.6, wherein the molar ratio of the silicon source to the aluminum source is in terms of molar ratio of silicon oxide to aluminum oxide, the molar ratio of the silicon source to the water in terms of molar ratio of silicon oxide to the water, and the molar ratio of the silicon source to the first structure directing agent in terms of molar ratio of silicon oxide to the first structure directing agent.

The calcination in step (a) is preferably carried out at a temperature of about 450° C. to about 600° C. for about 3 hours to about 15 hours. The calcination in step (b) is preferably carried out at a temperature of about 450° C. to about 600° C. for about 3 hours to about 8 hours.

The alkali treatment in step (c) is preferably performed at a temperature of about 40° C. to about 80° C., and an alkali solution used for the alkali treatment is preferably one or more of sodium hydroxide, sodium carbonate, sodium bicarbonate, potassium hydroxide, potassium carbonate, potassium hydrogen carbonate, tetrapropyl ammonium hydroxide, tetraethylammonium hydroxide, and tetramethyl ammonium hydroxide solutions.

The present disclosure further provides use of the aromatization catalyst as described hereinabove or the aromatization catalyst prepared according to the process as described hereinabove for aromatization of a lower alkane.

The present disclosure provides an aromatization catalyst comprising an inorganic oxide and a modified Ga-ZSM-5 zeolite, which comprises a modified ZSM-5 zeolite with a hierarchical macro-meso-microporosity and gallium deposited in channels of and/or on surfaces of the modified ZSM-5 zeolite. The hierarchical porosity of the modified ZSM-5 zeolite in the catalyst can reduce diffusion resistance of products during the aromatization reaction, thereby retarding carbon depositing rate and substantially improving the stability and lifetime of the catalyst. Furthermore, the hierarchical porosity of the catalyst improves the gallium dispersion and the catalytic activity and selectivity of the catalyst.

The present disclosure also provides a process for preparing the aromatization catalyst as described hereinabove by using a ZSM-5 zeolite as the raw material. This process enables the ZSM-5 zeolite and thus the catalyst to have a unique channel structure and a hierarchical macro-meso-microporosity, which can reduce diffusion resistance of products during the aromatization reaction, thereby retarding carbon depositing rate and substantially improving the stability and lifetime of the catalyst. Furthermore, the gallium deposited on the modified ZSM-5 zeolite can improve the ability of the catalyst to catalyze the aromatization reaction of the lower alkanes such that the selectivity to the aromatic hydrocarbons can be increased.

The present disclosure further provides use of the aromatization catalyst as described hereinabove or the aromatization catalyst prepared according to the process as described hereinabove for aromatization of a lower alkane. Results of examples show that, when the provided aromatization catalyst is used for the aromatization of propane, it exhibits a very high stability and a lifetime of up to about 320 hours, and can provide a selectivity to aromatic hydrocarbons of up to about 73.3%.

DRAWINGS

DETAILED DESCRIPTION

Figure 1:
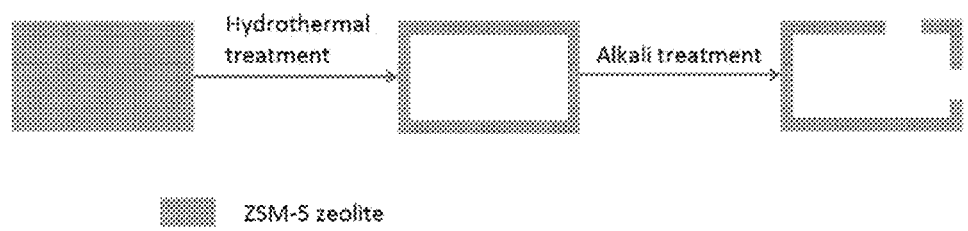
FIG. 1 is a schematic diagram showing the principle of a hydrothermal treatment and an alkali treatment according to the disclosure.

The present disclosure provides an aromatization catalyst comprising an inorganic oxide and a modified Ga-ZSM-5 zeolite, which comprises a modified ZSM-5 zeolite with a hierarchical macro-meso-microporosity and gallium deposited in channels of and/or on surfaces of the modified ZSM-5 zeolite.

The disclosed catalyst comprises an inorganic oxide. In some embodiments, the inorganic oxide is one or more of SB powder, dry glue powder, aluminum sol, kaolin, and pseudo-boehmite. In some embodiments, the mass of the inorganic oxide is preferably about 15 wt. % to about 70 wt. %, more preferably about 40 wt. % to about 70 wt. % of the mass of the catalyst. The inorganic oxide may act as a binder to bind the modified ZSM-5 zeolite and may allow for an increased selectivity to aromatic hydrocarbons, an improved stability, and a prolonged lifetime of the catalyst.

The disclosed catalyst comprises a modified Ga-ZSM-5 zeolite. Preferably, the mass of the modified Ga-ZSM-5 zeolite is about 30 wt. % to about 85 wt. %, more preferably about 40 wt. % to about 70 wt. % of the mass of the catalyst. In some embodiments, the modified Ga-ZSM-5 zeolite has an average grain size of about 150 nanometers to about 1000 nanometers. According to the disclosed catalyst, the modified Ga-ZSM-5 zeolite comprises a modified ZSM-5 zeolite with a hierarchical macro-meso-microporosity and gallium deposited in channels of and/or on surfaces of the modified ZSM-5 zeolite. In some embodiments, the micropores have an average pore size of less than about 2 nanometers. In some embodiments, the mesopores have an average pore size of about 2 nanometers to about 50 nanometers, preferably about 3 nanometers to about 10 nanometers, further preferably about 4 nanometers to about 7 nanometers. In some embodiments, the macropores have an average pore size of greater than about 50 nanometers. The hierarchical porosity of the modified ZSM-5 zeolite can reduce diffusion resistance of products during the aromatization reaction, thereby retarding carbon depositing rate and substantially improving the stability and lifetime of the catalyst. Furthermore, such hierarchical porosity can enhance the gallium dispersion so that the catalytic activity and selectivity to the aromatic hydrocarbons of the catalyst can be increased.

In some embodiments, the modified Ga-ZSM-5 zeolite has a gallium loading of about 0.1 wt. % to about 5 wt. %, preferably about 0.2 wt. % to about 2 wt. %. According to the disclosed catalyst, the gallium may act as a catalytic active component to catalyze the aromatization reaction. It has been found that the gallium atoms, in the form of individual atoms or small clusters, are located in channels of and/or on surfaces of the modified ZSM-5 zeolite, and are absent in the framework of the zeolite.

In some embodiments, the catalyst has a specific surface area of about 300 m$^2$/g to about 500 m$^2$/g, preferably about 350 m$^2$/g to about 450 m$^2$/g.

The disclosure further provides a process for preparing the aromatization catalyst as described hereinabove, comprising steps of:

(a) adding a silicon source into a mixed aqueous solution containing an aluminum source and a first structure directing agent to perform a hydrothermal reaction so as to obtain a first solid product, which is then subjected to calcination to obtain a ZSM-5 zeolite precursor;

(b) mixing the ZSM-5 zeolite precursor with water and a second structure directing agent together to perform a hydrothermal treatment so as to obtain a second solid product, which is then subjected to calcination;

(c) subjecting a product resulting from the calcination in step (b) to an alkali treatment so as to obtain a hierarchical ZSM-5 zeolite;

(d) subjecting the obtained zeolite to be modified with ammonium ions and to be calcined to obtain a modified ZSM-5 zeolite;

(e) subjecting the modified ZSM-5 zeolite to be ion-exchanged with a solution of gallium salt and then to be calcined to obtain a modified Ga-ZSM-5 zeolite; and (f0 mixing the modified Ga-ZSM-5 zeolite with an inorganic oxide precursor, followed by shaping, drying, and then calcination, to yield the catalyst.

According to the disclosed process, a silicon source is added into a mixed aqueous solution containing an aluminum source and a first structure directing agent to perform a hydrothermal reaction so as to obtain a first solid product, which is then calcined to yield a ZSM-5 zeolite precursor.

In particular, a silicon source is added into a mixed aqueous solution containing an aluminum source and a first structure directing agent to form a precursor solution. In some embodiments, a molar ratio of the silicon source to the aluminum source is about 20:1 or more, preferably about 30:1 to about 400:1, further preferably about 30:1 to about 300:1; a molar ratio of the water to the silicon source is about 10:1 to about 100:1, preferably about 20:1 to about 50:1, further preferably about 30:1; a molar ratio of the silicon source to the first structure directing agent is about 1:0.02 to about 1:0.6, preferably about 1:0.05 to about 1:0.5; wherein the molar ratio of the silicon source to the aluminum source is in terms of molar ratio of silicon oxide to aluminum oxide, the molar ratio of the silicon source to the water in terms of molar ratio of silicon oxide to the water, and the molar ratio of the silicon source to the first structure directing agent in terms of molar ratio of silicon oxide to the first structure directing agent.

In some embodiments, the silicon source is one or more of tetraethyl orthosilicate, tetramethoxysilane, tetrapropoxysilane, white carbon, and silica sol, preferably tetraethyl orthosilicate, tetramethoxysilane, or tetrapropoxysilane. In some embodiments, the aluminum source is sodium metaaluminate, aluminium nitrate, or aluminium sulfate. In some embodiments, the first structure directing agent is ethylenediamine, n-butylamine, tetrapropylammonium chloride, tetrapropylammonium bromide, or tetrapropyl ammonium hydroxide solutions, preferably tetrapropyl ammonium hydroxide, tetrapropylammonium bromide, or tetrapropylammonium chloride solutions.

In some embodiments, the precursor solution further contains an inorganic base. A preferable molar ratio of the inorganic base to the silicon source may be about 0.5:1 or less, more preferably from about 0.01:1 to about 0.3:1, wherein the molar ratio of the inorganic base to the silicon source is in terms of molar ratio of the inorganic base to silicon oxide. In some embodiments, the inorganic base is sodium hydroxide, potassium hydroxide, sodium carbonate, sodium bicarbonate, potassium carbonate, or potassium hydrogen carbonate.

The silicon source may be added into the mixed aqueous solution in any manner as long as it provides a uniform precursor solution. Preferably, the silicon source is added into the mixed aqueous solution containing the aluminum source and the first structure directing agent under stirring, and stirring is further conducted for about 1 hour to about 24 hours to provide a uniform precursor solution.

In embodiments where the precursor solution further contains the inorganic base, the silicon source is preferably added into a mixed aqueous solution containing the aluminum source, the inorganic base, and the first structure directing agent under stirring.

According to the process of the disclosure, after the precursor solution is obtained, it is subjected to a hydrothermal reaction. In some embodiments, the hydrothermal reaction is carried out at a temperature of about 120° C. to about 200° C., preferably about 140° C. to about 180° C., for about one day to about six days, preferably about two days to about five days. During the hydrothermal reaction, the first structure directing agent enables nucleation and crystallization to occur in the precursor solution, so that a crystalline ZSM-5 zeolite can be finally produced.

According to the process of the disclosure, after completion of the hydrothermal reaction, a first solid product thereof is subjected to calcination so as to obtain a ZSM-5 zeolite precursor. In some embodiments, the calcination is carried out at a temperature of about 450° C. to about 600° C., preferably about 500° C. to about 600° C. for about 2 hours to about 15 hours, preferably about 5 hours to about 10 hours. In an embodiment, the calcination is carried out in air atmosphere.

Preferably, a mixture resulting from the hydrothermal reaction is successively subjected to centrifugation, washing, and drying so as to obtain the first solid product of the hydrothermal reaction. The centrifugation and washing are not particularly limited, and may be performed in any manner known to those skilled in the art. In some embodiments, a resulting solid collected by centrifugation is washed until neutral. In some embodiments, the drying is performed at a temperature of about 40° C. to about 150° C., preferably about 60° C. to about 120° C. for about 8 hours to about 12 hours.

According to the process of the disclosure, the ZSM-5 zeolite precursor is mixed with water and a second structure directing agent together to perform a hydrothermal treatment so as to give a second solid product, which is then subjected to calcination.

In particular, the ZSM-5 zeolite precursor is mixed with water and a second structure directing agent together to form a mixture. Preferably, the second structure directing agent is the same as the first structure agent used in the preparation of the ZSM-5 zeolite precursor. In some embodiments, a ratio of the ZSM-5 zeolite precursor to the water is about 1 g:about 1-10 mL, preferably about 1 g:about 3-5 mL. In some embodiments, a ratio of the ZSM-5 zeolite precursor to the second structure directing agent is about 1 g:about 1-10 mL, preferably about 1 g:about 3-5 mL.

In some embodiments, the mixture further comprises an inorganic base and an aluminum source. Preferably, the inorganic base and the aluminum source are the same as those used in the preparation of the ZSM-5 zeolite precursor, and will not be described here in detail. In some embodiments, a molar ratio of the inorganic base to silicon in the ZSM-5 zeolite precursor is about 0.5:1 or less, preferably about 0.01:1 to about 0.3:1. In some embodiments, a molar ratio of the aluminum source in terms of the aluminum atoms to silicon in the ZSM-5 zeolite precursor is about 0.05:1 or less, preferably about 0.00001:1 to about 0.03:1, wherein the silicon content in the ZSM-5 zeolite precursor refers to the content of the silicon atoms therein, and may be obtained with measurement. The mixing is not particularly limited, and may be conducted in any manner known to those skilled in the art. Preferably, before mixing, the ZSM-5 zeolite precursor is ground into powder.

According to the process of the disclosure, the mixture is then subjected to a hydrothermal treatment. In some embodiments, the hydrothermal treatment is performed at a temperature of about 120° C. to about 200° C., preferably about 140° C. to about 180° C. for about one day to about four days, preferably about one day to about three days. During the hydrothermal treatment, the ZSM-5 zeolite precursor is recrystallized under the action of the second structure directing agent after dissolution of part of silicon and aluminum ions to form a ZSM-5 zeolite having a hollow structure (i.e., having macropores). The Si/Al ratios before and after the hydrothermal treatment are almost the same.

Preferably, a resulting mixture of the hydrothermal treatment is successively subjected to centrifugation, washing, and drying so as to obtain a second solid product. The centrifugation and washing are not particularly limited, and may be conducted in any manner known to those skilled in the the art. In some embodiments, a resulting solid collected by centrifugation is washed until neutral. In some embodiments, the drying is performed at a temperature of about 40° C. to about 150° C., preferably about 60° C. to about 120° C. for about 3 hours to about 15 hours.

According to the process of the disclosure, after the second solid product is obtained, it is subjected to calcination. In some embodiments, the calcination is carried out at a temperature of about 450° C. to about 600° C., preferably about 500° C. to about 600° C. for about 1 hour to about 24 hours, preferably about 3 hours to about 15 hours, further preferably about 5 hours to about 10 hours. During the calcination, the second structure directing agent may be removed from the framework of the second solid product to form micropores therein. This enables the ZSM-5 zeolite to have micropores besides the macropores.

According to the process of the disclosure, after the calcination is completed, a resulting product is subjected to an alkali treatment. In some embodiments, the alkali solution used for the alkali treatment is one or more of sodium hydroxide, sodium carbonate, sodium bicarbonate, potassium hydroxide, potassium carbonate, potassium hydrogen carbonate, tetrapropyl ammonium hydroxide, tetraethylammonium hydroxide, and tetramethyl ammonium hydroxide solutions. In some embodiments, the alkali treatment is performed at a temperature of about 30° C. to about 100° C., preferably about 40° C. to about 100° C. In some embodiments, a specific time required for the alkali treatment is determined by the kind of the alkali solutions. In the case that sodium hydroxide solution and/or potassium hydroxide solution is used as the alkali solution, the alkali solution preferably has a concentration of about 0.005 mol/L to about 0.3 mol/L and the alkali treatment is preferably performed for about 5 minutes to about 100 minutes. In the case that the alkali solution is one or more of sodium carbonate, potassium carbonate, sodium bicarbonate, potassium hydrogen carbonate, tetrapropyl ammonium hydroxide, tetraethylammonium hydroxide, and tetramethyl ammonium hydroxide solutions, the alkali solution preferably has a concentration of about 0.01 mol/L to about 5.0 mol/L, and the alkali treatment is preferably performed for about 10 minutes to about 300 minutes. The alkali treatment enables mesopores to be formed in an outer shell of the ZSM-5 zeolite having macropores, so that a macro-meso-microporous ZSM-5 zeolite can be obtained. FIG. 1 illustrates the specific principle. Since mesopores have been formed in the outer shell of the ZSM-5 zeolite having macropores, when Ga species are incorporated into the zeolite, they can diffuse inside cavities through the mesopores. This enables an enhanced dispersion of the Ga species. Furthermore, aromatic hydrocarbons produced during the aromatization reaction can easily diffuse out of the mesopores, thereby allowing the catalyst to have improved resistance to carbon depositing.

After the alkali treatment is completed, preferably, a resulting mixture thereof is subjected to centrifugation, washing, and drying so as to obtain a hierarchical ZSM-5 zeolite. The centrifugation and washing are not particularly limited, and may be conducted in any manner known to those skilled in the art. In some embodiments, a resulting solid collected by centrifugation is washed until neutral. In some embodiments, the drying is carried out at a temperature of about 40° C. to about 150° C., preferably about 60° C. to about 120° C., for about 3 hours to about 15 hours.

According to the process of the disclosure, after the hierarchical ZSM-5 zeolite is obtained, it is modified with ammonium ions and then calcined to obtain a modified ZSM-5 zeolite.

In particular, the hierarchical ZSM-5 zeolite is modified with ammonium ions. In some embodiments, this modification is conducted at a temperature of about 50° C. to about 100° C., preferably about 70° C. to about 85° C. for about 2 hours to about 15 hours, further preferably about 6 hours to about 12 hours. In some embodiments, the solution containing the ammonium ions used for this modification is one or more of ammonium nitrate, ammonium chloride, ammonium sulfate, and ammonium carbonate solutions. Preferably, the solution containing the ammonium ions has a concentration of about 0.1 mol/L to about 3 mol/L, further preferably about 0.5 mol/L to about 2 mol/L. In some embodiments, the ZSM-5 zeolite is dispersed into the solution containing the ammonium ions under stirring. In some embodiments, a solid/liquid ratio of the ZSM-5 zeolite to the solution containing the ammonium ions is about 1 g:about 5 to 60 mL, preferably about 1 g:about 20 to 40 mL. The stirring rate is not particularly limited as long as no liquid splashing may occur. In some embodiments, the modification is conducted more than one times to achieve a better modifying effect of the zeolite. In these embodiments, the modification period as described hereinabove refers to the total time period of the modification, and the modification period is preferably the same each time modification is conducted. Further, in these embodiments, the above-mentioned solid/liquid ratio refers to the ratio of the ZSM-5 zeolite subjected to a single modification to the solution containing the ammonium ions used for the single modification. During the modification, sodium ions from the ZSM-5 zeolite exchange with ammonium ions in the solution. It has been found that the zeolite after the ion exchange is acidic, and if such modification is not performed, the catalyst so obtained will exhibit no activity.

In some embodiments, the calcination is performed at a temperature of about 450° C. to about 600° C., preferably about 500° C. to about 550° C. for about one hour to about 10 hours, preferably about 4 hours to about 8 hours. The calcination causes the ammonium ions ($NH_4^+$) to decompose into hydrogen ions ($H^+$) and ammonia gas ($NH_3$). During the calcination, the resulting ammonia gas is removed, and the hydrogen ions are left.

Preferably, before the calcination, a product resulting from the modification is dried. In some embodiments, the drying is conducted at a temperature of about 40° C. to about 150° C., preferably about 60° C. to about 120° C., for about 3 hours to about 15 hours.

According to the process of the disclosure, after the modified ZSM-5 zeolite is obtained, it is subjected to ion exchange with a solution of gallium salt and then to calcination to obtain a modified Ga-ZSM-5 zeolite.

In some embodiments, the solution of gallium salt is gallium chloride, gallium nitrate, or gallium sulfate solutions. In some embodiments, the solution has a concentration of about 5 mol/L or less, preferably about 2 mol/L or less. In some embodiments, the gallium ions in the solution has a mass corresponding to that of the gallium loaded in the catalyst as described hereinabove. In some embodiments, the modified ZSM-5 zeolite is dispersed into the solution under stirring to perform the ion exchange. The stirring rate is not particularly limited as long as no liquid splashing may occur. In some embodiments, the ion exchange is performed at a temperature of about 60° C. to about 100° C. for about 3 hours to about 15 hours. During the ion exchange, the gallium ions are exchanged with the hydrogen ions, and are allowed to enter into the channels of the modified Ga-ZSM-5 zeolite and/or be adsorbed on the surfaces of the zeolite.

In some embodiments, the calcination is performed at a temperature of about 400° C. to about 600° C., preferably about 450° C. to about 550° C. for about one hour to about 10 hours, preferably about 3 hours to about 6 hours. The calcination process can remove water from the products thereof.

Preferably, before the calcination, a product resulting from the modification is dried. In some embodiments, the drying is conducted at a temperature of about 40° C. to about 150° C., preferably about 60° C. to about 120° C. for about 3 hours to about 15 hours.

According to the process of the disclosure, after the modified Ga-ZSM-5 zeolite is obtained, it is mixed with an inorganic oxide precursor, followed by shaping, drying, and then calcination, to obtain the catalyst.

In some embodiments, the inorganic oxide precursor is one or more of SB powder, dry glue powder, aluminum sol, kaolin, and pseudo-boehmite. In some embodiments, the amount of the inorganic oxide precursor used is determined according to the content of the inorganic oxide in the final catalyst. The shaping and drying are not particularly limited, and may be conducted in any manner known to those skilled in the art. In some embodiments, the calcination is performed at a temperature of about 500° C. to about 550° C. for about 2 hours to about 10 hours. The calcination process enables the modified Ga-ZSM-5 zeolite to be more firmly bonded with the inorganic oxide. The inorganic oxide precursor may act as a binder during the shaping, and can increase the selectivity to the aromatic hydrocarbons, the stability and lifetime of the catalyst.

The disclosure yet further provides the use of the aromatization catalyst as described hereinabove or the aromatization catalyst prepared according to the process as described hereinabove for aromatization of a lower alkane.

In some embodiments, the lower alkane is one or more of $C_2$-$C_4$ alkanes, preferably propane and butane. In some embodiments, the aromatization is carried out at a temperature of about 500° C. to about 550° C. under normal pressure at a weight hourly space velocity of about 0.3 $h^{-1}$ to about 2 $h^{-1}$.

The aromatization catalyst, and the preparation process and use thereof according to the disclosure will now be described in more details with reference to particular examples, which are not intended to limit the disclosure in any way.

Example 1

(1) 0.1822 g of sodium metaaluminate, 38.75 g of deionized water, 20.336 g of 25 wt. % aqueous tetrapropyl ammonium hydroxide solution, and 0.1 g of sodium hydroxide were introduced into a beaker and stirred until a clear solution had been obtained. Then, 20.833 g of tetraethyl orthosilicate was slowly added dropwise thereto. Thereafter, after being stirred for 12 hours, the solution was transferred to a hydrothermal reactor, and heated at 170° C. for 4 days to conduct crystallization. After crystallization, centrifugation was conducted. The mother liquor resulting therefrom was removed, and the precipitate resulting therefrom was washed with deionized water until neutral. The washed solid was dried at 100° C. overnight, and then calcined at 600° C. for 10 hours to obtain a ZSM-5 zeolite precursor.

(2) The obtained zeolite precursor was ground into powder. 1 g of the zeolite precursor powder (with 0.4 g of silicon determined by measurement), 0.01 g of sodium hydroxide and 0.002 g of sodium metaaluminate were dispersed into 5 mL of water and 3 mL of 1 mol/L tetrapropyl ammonium hydroxide solution. Thereafter, after being stirred for 10 minutes, the resulting solution was transferred to a hydrothermal reactor, and heated at 170° C. for one day to conduct a hydrothermal treatment. After the hydrothermal treatment, centrifugation was conducted. The mother liquor resulting therefrom was removed, and the precipitate resulting therefrom was washed with deionized water until neutral. The washed solid was dried at 100° C. overnight, and then calcined at 600° C. for 6 hours to obtain a ZSM-5 zeolite with macro-microporosity.

(3) The obtained ZSM-5 zeolite with macro-microporosity was treated with 0.005 mol/L to 0.5 mol/L sodium hydroxide solution at 60° C. to 65° C. for 15 minutes. Then, centrifugation was conducted. The mother liquor resulting therefrom was removed, and the precipitate resulting therefrom was washed with deionized water until neutral. The washed solid was dried at 100° C. overnight to obtain a hierarchical ZSM-5 zeolite.

(4) The obtained zeolite was ion-exchanged with 1 mol/L ammonium nitrate solution at 80° C. for 4 hours twice. Then, centrifugation was conducted. The mother liquor resulting therefrom was removed, and the precipitate resulting therefrom was washed three times with deionized water. The washed solid was dried at 100° C. overnight, and calcined at 550° C. for 6 hours to obtain a modified ZSM-5 zeolite.

(5) The modified ZSM-5 zeolite obtained was ion-exchanged with gallium nitrate solution such that the gallium was present in an amount of 0.5 wt. % based on the total weight of the modified ZSM-5 zeolite. The ion-exchanged zeolite was dried at 100° C. overnight and then calcined at 550° C. for 4 hours to obtain a modified Ga-ZSM-5 zeolite.

(6) 14 g of the modified Ga-ZSM-5 zeolite was mixed with 6 g of SB powder in a known manner, followed by shaping, drying, and then calcination at 550° C. for 6 hours, to obtain an aromatization catalyst, labeled as Catalyst 1 #.

Example 2

An aromatization catalyst was prepared in the same manner as in Example 1, except that: (a) the weight of sodium metaaluminate was 0.3279 g; (b) sodium hydroxide was replaced by sodium carbonate; and (c) the alkali treatment was performed for 6 hours. The catalyst so obtained was labeled as Catalyst 2 #.

Figure 2:
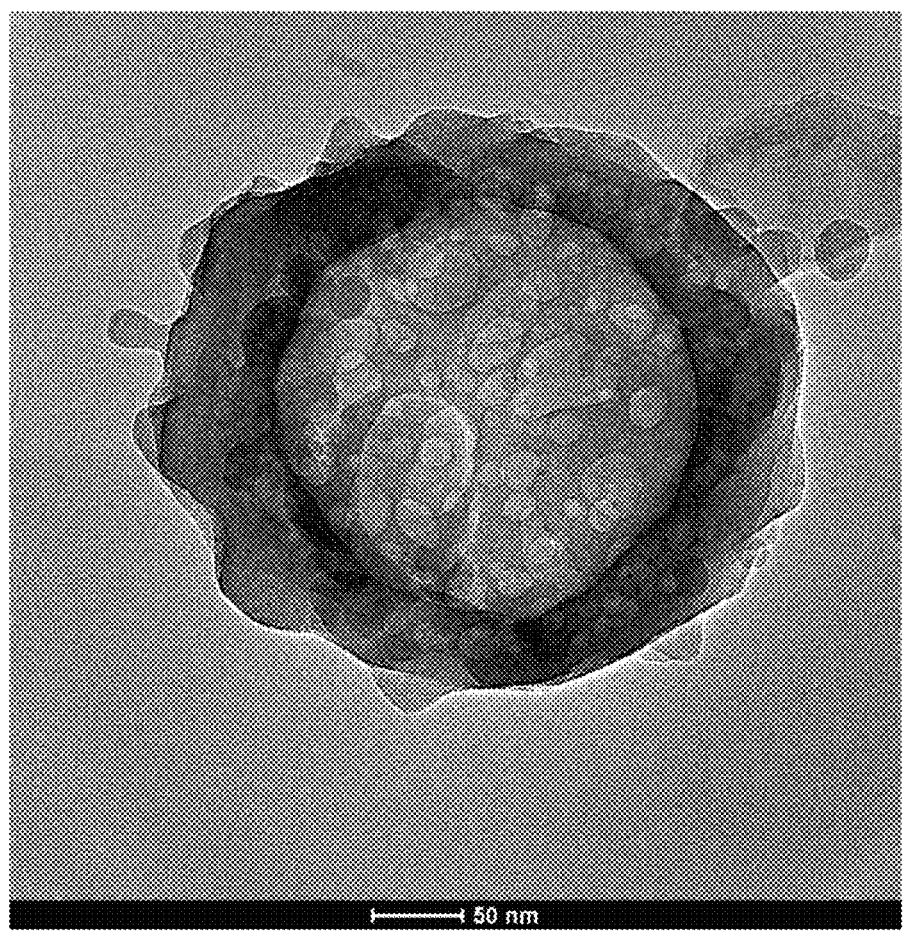
FIG. 2 shows a TEM image of a catalyst in Example 2.

Catalyst 2 # was observed by field emission transmission electron microscope JEM 2100-F produced by Rigaku Corporation. The result is shown in FIG. 2. This figure shows that the catalyst had hierarchical pores.

Figure 3:
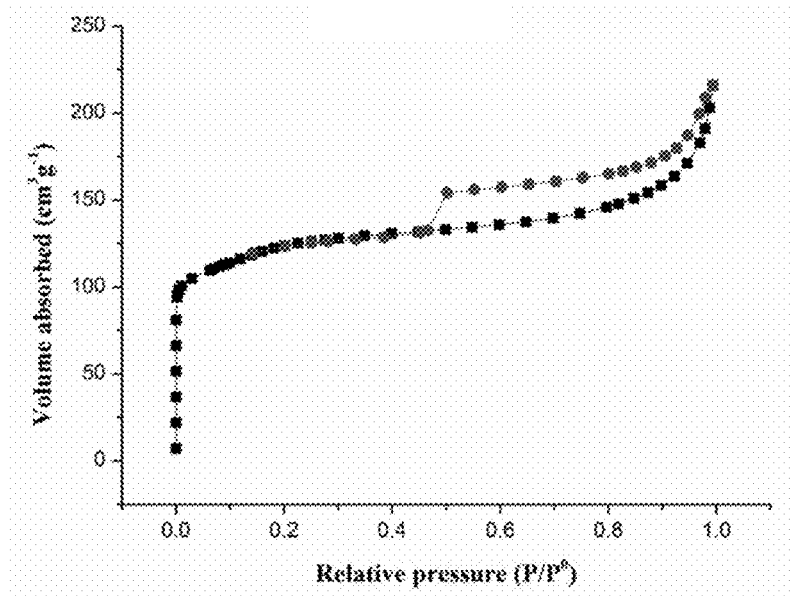
FIG. 3 shows a BET adsorption isotherm of the catalyst in Example 2.

Adsorption test was conducted on Catalyst 2 #, and the resulting adsorption isotherm is shown in FIG. 3. This figure shows that the catalyst had a BET specific surface area of 392 $m^2/g$, and a pore volume of 0.40 $cm^3/g$, with a micropore volume of 0.085 $cm^3/g$.

Figure 4:
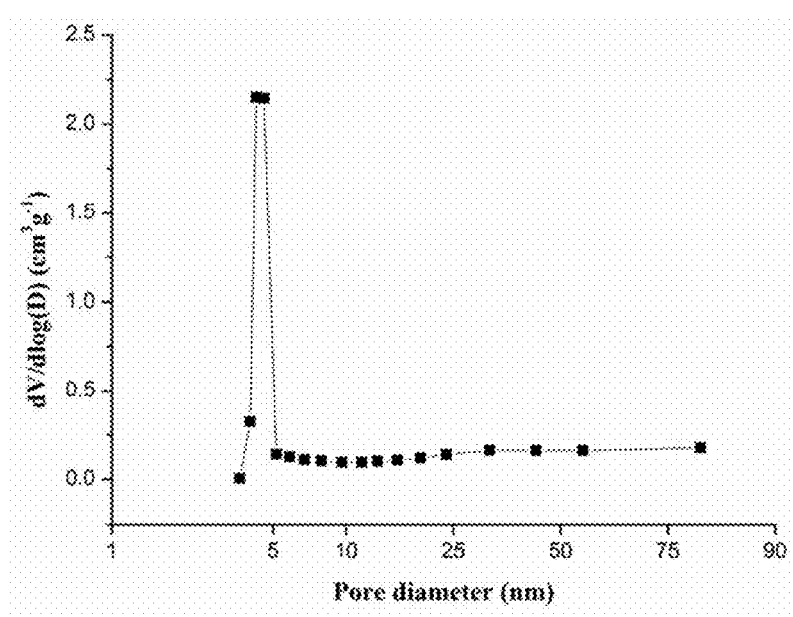
FIG. 4 is a graph of the pore size distribution of the catalyst in Example 2.

Pore size analysis was conducted on Catalyst 2 #, and the resulting pore size distribution is shown in FIG. 4. This figure shows that Catalyst 2 # had an average mesoporous pore size of around 4 nanometers.

Example 3

An aromatization catalyst was prepared in the same manner as in Example 1, except that: (a) sodium hydroxide was not used in step (1); and (b) sodium hydroxide and sodium metaaluminate were not used in step (2). The catalyst so obtained was labeled as Catalyst 3 #.

Comparative Example 1

An aromatization catalyst was prepared in the same manner as in Example except that neither the hydrothermal treatment in step (2) nor the alkali treatment in step (3) was performed.

In particular, 0.1822 g of sodium metaaluminate, 38.75 g of deionized water, and 20.336 g of 25 wt. % aqueous tetrapropyl ammonium hydroxide solution were introduced into a beaker and stirred until a clear solution had been obtained. Then, 20.833 g of tetraethyl orthosilicate was slowly dropwise added thereto. Thereafter, the solution was transferred to a hydrothermal reactor, and heated at 170° C. for 4 days to conduct crystallization. After crystallization, centrifugation was conducted. The mother liquor resulting therefrom was removed, and the precipitate resulting therefrom was washed with deionized water until neutral. The washed solid was dried at 100° C. overnight, and then calcined at 600° C. for 10 hours to obtain a ZSM-5 zeolite precursor. The obtained zeolite precursor was ground into powder, and was ion-exchanged with ammonium nitrate solution according to step (4) in Example 1 and then with gallium nitrate solution according to step (5) such that the gallium was present in an amount of 0.5 wt. % based on the total weight of the carrier. The resulting solid was dried at 100° C. overnight and then calcined at 550° C. for 4 hours. A catalyst, labeled as Catalyst 4 #, was finally obtained according to step (6).

The content of the modified Ga-ZSM-5 zeolite in each of Catalysts 1 #, 2 #, 3 #, and 4 # was controlled to be around 70 wt. %.

Reaction Examples

Catalysts 1 #, 2 #, 3 #, and 4 # were each used in the aromatization reaction of propane. The reaction was carried out at 540° C. under normal pressure at a weight hourly space velocity (WHSV) of 0.9 h$^{-1}$. Reaction products were subjected to gas-liquid separation by a condenser. Gas and liquid phase products were analyzed by gas chromatography (Agilent 7820A), wherein fractions of various components were in terms of weight fractions thereof. Reaction results are shown in Table 1.

TABLE 1

Evaluation Results of the Prepared Catalysts

| | | Catalyst 1# | Catalyst 2# | Catalyst 3# | Catalyst 4# |
|---|---|---|---|---|---|
| Propane Conv. (wt. %) | | 51 | 63 | 50 | 49 |
| Product Sel. (wt. %) | Benzene | 21.6 | 24.7 | 19.8 | 14.3 |
| | Toluene | 29.6 | 27.9 | 25.6 | 17.6 |
| | Xylenes | 10.8 | 10.5 | 10.4 | 5.5 |
| | Ethylbenzene | 1.4 | 1.9 | 1.0 | 0.6 |
| | Heavy aromatic hydrocarbons | 6.5 | 8.3 | 7.2 | 3.1 |
| | non-aromatic hydrocarbons | 30.1 | 26.7 | 36.0 | 58.9 |

Table 1 shows that, as compared with Catalysts 1 # and 2 # in Examples 1 and 2, respectively, Catalyst 4 #, a conventional catalyst that had not been subjected to the hydrothermal and alkali treatments, had an aromatic hydrocarbon selectivity of only 41.1%, while Catalyst 2 # had an aromatic hydrocarbon selectivity of 73.3%.

Figure 5:
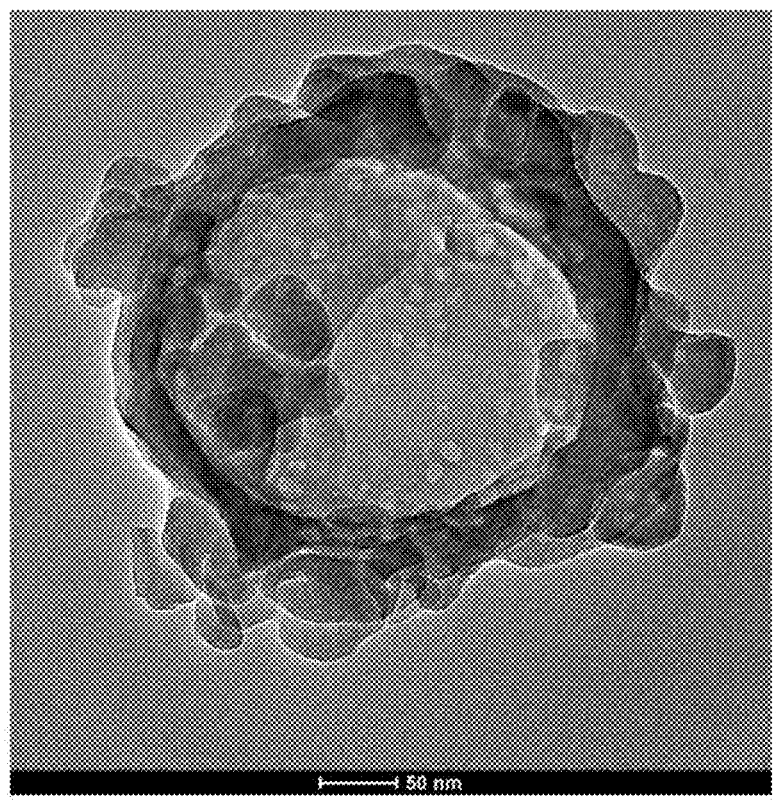
FIG. 5 shows a TEM image of the catalyst in Example 2 after reaction.

A transmission electron microscopy (TEM) micrograph of the used catalyst 2 # is shown in FIG. 5. This figure shows that no changes in the structure and the morphology of the catalyst occurred before and after the aromatization reaction, i.e., the structural integrity of the catalyst was maintained during the reaction. This indicates that the catalyst had an excellent thermal stability.

Catalyst Recycling

Figure 6:
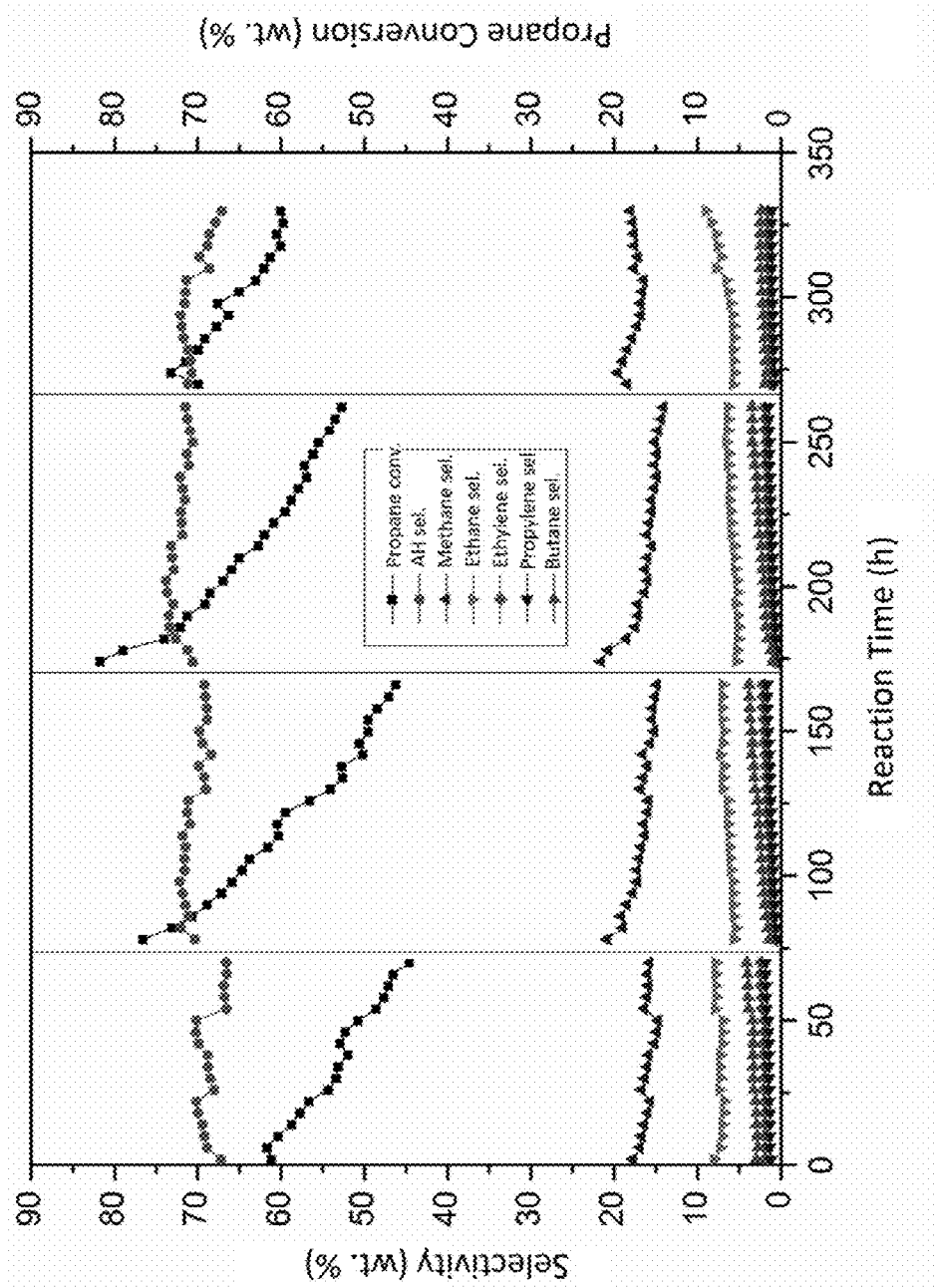
FIG. 6 shows results of aromatization of propane catalyzed by the catalyst in Example 2 at 540° C.

After 75 hours, 170 hours, and 270 hours of aromatization using Catalyst 2 #, the deactivated catalyst 2 # was regenerated by calcining at 540 to 550° C. in a flowing air atmosphere for 6 to 12 hours. Thereafter, the regenerated catalyst was subjected again to an aromatization reaction of propane at 540° C., and its specific reaction conditions were the same as in the case of the fresh catalyst. Reaction results are shown in FIG. 6. This figure shows that the catalyst had an aromatic hydrocarbon selectivity of around 70% up to 73%. These results indicate that the catalyst had a high selectivity to the aromatic hydrocarbons and exhibited good stability. Each vertical line such as at 75 h and 170 h in FIG. 6 represents a single regeneration process. It can be seen from this figure that the regenerated catalyst enabled the conversion of propane to be restored to a high level, which is even higher than that provided by the fresh catalyst. This indicates that the catalyst was excellent in recyclability. The catalyst had a lifetime of more than 320 hours.

These examples demonstrate that the catalyst of the disclosure, when used for the aromatization of a lower alkane, exhibited a high catalytic activity, a high selectivity, good thermal stability, a long lifetime and good recyclability.

The descriptions above are just preferred embodiments of the disclosure. It should be noted that, for those skilled in the art, various improvements and embellishments of the embodiments described herein can be made without departing from the principles of the disclosure and should be considered to fall within the scope of the disclosure.

What is claimed is:

1. An aromatization process for producing aromatic hydrocarbons from a lower alkane, comprising: contacting the lower alkane with an aromatization catalyst consisting of an inorganic oxide and a modified Ga-ZSM-5 zeolite consisting of a modified ZSM-5 zeolite with a hierarchical macro-meso-microporosity and gallium deposited in channels of or on surfaces of the modified ZSM-5 zeolite, or both;

wherein the aromatization is carried out at a temperature of 500° C. to 550° C. under normal pressure at a weight hourly space velocity of 0.3 h$^{-1}$ to 2 h$^{-1}$, wherein a process for preparing the aromatization catalyst comprises:

(a) adding a silicon source into a mixed aqueous solution containing an aluminum source and a first structure directing agent to perform a hydrothermal reaction so as to obtain a first solid product, which is then subjected to calcination to obtain a ZSM-5 zeolite precursor;

(b) mixing the ZSM-5 zeolite precursor with water and a second structure directing agent together to perform a hydrothermal treatment so as to obtain a second solid product, which is then subjected to calcination;

(c) subjecting a product resulting from the calcination in step (b) to an alkali treatment so as to obtain a hierarchical ZSM-5 zeolite;

(d) subjecting the obtained zeolite to be modified with ammonium ions and then calcined to obtain the modified ZSM-5 zeolite;

(e) subjecting the modified ZSM-5 zeolite to be ion-exchanged with a solution of gallium salt and then to be calcined to obtain the modified Ga-ZSM-5 zeolite; and
(f) mixing the modified Ga-ZSM-5 zeolite with an inorganic oxide precursor, followed by shaping, drying, and then calcination, to yield the catalyst.

2. The process according to claim 1, wherein the lower alkane comprises one or more of $C_2$-$C_4$ alkanes.

3. The process according to claim 2, wherein the lower alkane is propane and/or butane.

4. The process according to claim 3, wherein the lower alkane is propane.

* * * * *